United States Patent
Richard et al.

(10) Patent No.: US 8,697,119 B2
(45) Date of Patent: *Apr. 15, 2014

(54) MEDICAL DEVICES AND MATERIALS CONTAINING ISOBUTYLENE COPOLYMER

(75) Inventors: Robert E. Richard, Wrentham, MA (US); Rudolf Faust, Lexington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1729 days.

This patent is subject to a terminal disclaimer.

(21) Appl. No.: 10/894,394

(22) Filed: Jul. 19, 2004

(65) Prior Publication Data

US 2006/0013867 A1    Jan. 19, 2006

(51) Int. Cl.
*A61K 9/70*    (2006.01)

(52) U.S. Cl.
USPC ........................................................ 424/449

(58) Field of Classification Search
USPC .................... 424/400, 422, 423, 424, 425
See application file for complete search history.

(56) References Cited

U.S. PATENT DOCUMENTS

| | | | |
|---|---|---|---|
| 6,306,419 B1 * | 10/2001 | Vachon et al. ................. | 424/422 |
| 6,310,165 B1 * | 10/2001 | Wang ............................. | 526/348 |
| 6,545,097 B2 * | 4/2003 | Pinchuk et al. ............... | 525/240 |
| 6,835,387 B2 * | 12/2004 | Herrmann ...................... | 424/425 |
| 6,974,851 B2 * | 12/2005 | Gronowski et al. ......... | 525/332.5 |
| 2002/0107330 A1 | 8/2002 | Pinchuk et al. | |
| 2002/0127327 A1 * | 9/2002 | Schwarz et al. ............. | 427/2.15 |
| 2003/0235602 A1 * | 12/2003 | Schwarz ........................ | 424/424 |
| 2003/0236514 A1 | 12/2003 | Schwarz ...................... | 604/890.1 |
| 2004/0106987 A1 * | 6/2004 | Palasis et al. ................. | 623/1.42 |
| 2004/0110904 A1 * | 6/2004 | Gronowski et al. ........... | 525/263 |
| 2005/0037048 A1 * | 2/2005 | Song ............................. | 424/423 |

FOREIGN PATENT DOCUMENTS

WO    WO 2004/000380 A1    12/2003    .............. A61L 27/34

OTHER PUBLICATIONS

Judit E. Puskas, et al., "Polyisobutylene-Based Biomaterials", *Journal of Polymer Science, Part A: Polymer Chemistry*, vol. 42, No. 13, Jul. 1, 2004, pp. 3091-3190.
Matyjaszewski, Krzysztof. "Well-Defined (Co)Polymers by Atom Transfer Radical Polymerization". Polymer Preprints. vol. 43. No. 2. p. 34-35. 2002.
Lutz, Jean-Francois; Matyjaszewski, Krzysztof. "Synthesis of Graft Terpolymers Poly (Alkyl Methacrylate)-G-Poly (D-Lactic Acid)/Poly (Dimethyl Siloxane) Using the Grafting Through Method in Atom Transfer Radical Polymerization". Polymer Preprints. vol. 43. No. 2. 2002. pp. 231-232.
Tsarevsky, Nicolay V.; Jia, Shijun; Tang, Chuanbing; Kowalewski, Tomasz; Matyjaszewski, Krzysztof. "Synthesis of Block Copolymers of Acrylonitrile and N-Butyl Acrylate by Atom Transfer Radical Polymerization, Morphological Studies by Atomic Force Microscopy". Polymer Preprints. vol. 43. No. 2. 2002. pp. 207-208.
Matyjaszewski, Krzysztof; Shipp, Devon A.; Mcmurtry, Gabriel P.; Gaynor, Scott G.; Pakula, Tadeusz. "Simple and Effective One-Pot Synthesis of (Meth) Acrylic Block Copolymers Through Atom Transfer Radical Polymerization". Journal of Polymer Science: Part A: Polymer Chemistry. vol. 38. 2000. pp. 2023-2031.
Shipp, Devon A.; Wang, Jen-Lung. Matyjaszewski, Krzysztof. "Synthesis of Acrylate and Methacrylate Block Copolymers Using Atom Transfer Radical Polymerization". Macromolecules. vol. 31. 1998. pp. 8005-8008.
David, Ghislain; Robin, Jean-Jacques; Desmazes-Lacroix, Patrick. "Synthesis of Thermoplastic Elastomer Based on Polystyrene Polydimethysiloxane Block Copolymers". Polymer Preprints. vol. 43. No. 2. 2002. pp. 1095-1096.
Matyjaszewski, Krzysztof; Ziegler, Michael J.; Arehart, Stephen V.; Greszta; Pakula, Tadeusz. "Gradient Copolymers by Atom Transfer Radical Copolymerization". J. Phys. Org. Chem. vol. 13. 2000. pp. 775-786.
Miller, Peter J.; Matyjaszewski, Krzysztof. "Atom Transfer Radical Polymerization of (Meth) Acrylates From Poly(Dimethylsiloxane) Macroinitiators". Macromolecules. vol. 32. 1999. 8760-8767.
Pyun, Jeffrey; Matyjaszewski. "Synthesis of Nanocomposite Organic/Inorganic Hybrid Materials Using Controlled/"Living" Radical Polymerization". Chem. Mater. vol. 13. 2001. pp. 3436-3448.
"Morphology of Block Copolymers". Block Copolymers and Thermoplastic Elastomers. pp. 282-287.

* cited by examiner

*Primary Examiner* — Scott Long
*Assistant Examiner* — Sarah Alawadi
(74) *Attorney, Agent, or Firm* — Fish & Richardson P.C.

(57) ABSTRACT

The present invention relates to medical devices which contain isobutylene copolymers. The present invention also relates to biocompatible copolymer materials for therapeutic agent delivery comprising a therapeutic-agent-loaded isobutylene copolymer. According to an aspect of the present invention, a medical device is provided, which includes: (a) a substrate and (b) at least one polymeric layer, which contains a copolymer, disposed over all or a portion of the substrate. The copolymer contains one or more polymer chains, within which isobutylene and elevated $T_g$ monomers (and, optionally, other monomers) are incorporated in a random, periodic, statistical or gradient distribution.

11 Claims, 1 Drawing Sheet

MEDICAL DEVICES AND MATERIALS CONTAINING ISOBUTYLENE COPOLYMER

FIELD OF THE INVENTION

The present invention relates to medical devices which contain isobutylene copolymers loaded with a therapeutic agent. The present invention also relates to biocompatible copolymer materials for therapeutic agent delivery comprising a therapeutic-agent-loaded isobutylene copolymer.

BACKGROUND OF THE INVENTION

As is well known, polymers are molecules containing one or more chains, which contain multiple copies of one or more constitutional units. An example of a common polymer is polyisobutylene, where n is an integer, typically an integer of 10 or more, more typically on the order of 10's, 100's, 1000's or even more, in which the constitutional units in the chain correspond to isobutylene monomers:

(i.e., they originate from, or have the appearance of originating from, the polymerization of isobutylene monomers, in this case the addition polymerization of isobutylene monomers). Copolymers are polymers that contain at least two dissimilar constitutional units.

Numerous polymer-based medical devices have been developed for the delivery of therapeutic agents to the body. In accordance with some typical delivery strategies, a therapeutic agent is provided within a polymeric carrier layer and/or beneath a polymeric barrier layer that is associated with a medical device. Once the medical device is placed at the desired location within a patient, the therapeutic agent is released from the medical device at a rate that is dependent upon the nature of the polymeric carrier and/or barrier layer.

Materials which are suitable for use in making implantable or insertable medical devices typically exhibit one or more of the qualities of exceptional biocompatibility, extrudability, elasticity, moldability, good fiber forming properties, tensile strength, durability, and the like. Moreover, the physical and chemical characteristics of the device materials can play an important role in determining the final release rate of the therapeutic agent.

As a specific example, block copolymers of polyisobutylene and polystyrene, for example, polystyrene-polyisobutylene-polystyrene triblock copolymers (SIBS copolymers), which are described in U.S. Pat. No. 6,545,097 to Pinchuk et al., which is hereby incorporated by reference in its entirety, have proven valuable as release polymers in implantable or insertable drug-releasing medical devices. As described in Pinchuk et al., the release profile characteristics of therapeutic agents such as paclitaxel from SIBS copolymer systems demonstrate that these copolymers are effective drug delivery systems for providing therapeutic agents to sites in vivo.

These copolymers are particularly useful for medical device applications because of their excellent strength, biostability and biocompatibility, particularly within the vasculature. For example, SIBS copolymers exhibit high tensile strength, which frequently ranges from 2,000 to 4,000 psi or more, and resist cracking and other forms of degradation under typical in vivo conditions. Biocompatibility, including vascular compatibility, of these materials has been demonstrated by their tendency to provoke minimal adverse tissue reactions (e.g., as measured by reduced macrophage activity). In addition, these polymers are generally hemocompatible as demonstrated by their ability to minimize thrombotic occlusion of small vessels when applied as a coating on coronary stents. Furthermore, these polymers possess many interesting physical and chemical properties sought after in medical devices, due to the combination of polymer blocks.

Although polymers are known for use in drug-releasing medical devices, there is a continuing need for novel polymeric materials that can serve as release layers in medical devices. In particular, it may be advantageous to provide polymers that, in addition to the biocompatibility, biostability, and physical and chemical properties of known block polymers such as SIBS, provide enhanced drug release characteristics from the release layer such as a linear and sustained release of the therapeutic agent instead of a burst release profile seen in prior art SIBS block copolymers.

SUMMARY OF THE INVENTION

These and other challenges of the prior art are addressed by the present invention which, in one aspect, provides medical devices that comprise (a) a substrate and (b) at least one polymeric layer comprising a copolymer disposed over the substrate, wherein the copolymer comprises a polymer chain that in turn comprises (i) an isobutylene monomer and (ii) at least one elevated $T_g$ monomer. The isobutylene and elevated $T_g$ monomers are incorporated into the polymer chain in a random, periodic, statistical or gradient distribution. The invention also provides a method of forming the above medical devices comprising: (a) providing a solution comprising (i) a solvent system and (ii) the copolymer; and (b) forming the polymeric layer from the solution by removing the solvent system from the solution.

In another aspect, the invention provides a composition for delivery of a therapeutic agent comprising: (a) a copolymer comprising a polymer chain that comprises (i) an isobutylene monomer and (ii) an elevated $T_g$ monomer, wherein the isobutylene and elevated $T_g$ monomer are incorporated into the polymer chain in a random, periodic, statistical or gradient distribution and (b) a therapeutic agent. The copolymer is loaded with the therapeutic agent.

One advantage of the present invention is that a variety of materials can be provided for use in release layers of implantable or insertable medical devices and for use in other therapeutic-agent-delivering compositions.

Another advantage of the present invention is that medical devices and therapeutic-agent-delivering compositions are provided which result in controlled release of a therapeutic agent.

Yet another advantage of the present invention is that polymeric materials are provided which are biostable and biocompatible for a variety of in vivo applications and which can provide a linear release of a therapeutic agent.

These and other embodiments and advantages of the present invention will become immediately apparent to those of ordinary skill in the art upon review of the Detailed Description and Claims to follow.

DETAILED DESCRIPTION OF THE INVENTION

The present invention relates to copolymers that are useful in connection with medical devices, such as an intravascular or intervascular medical device.

According to an aspect of the present invention, a medical device is provided, which includes: (a) a substrate and (b) a polymeric layer, which contains a copolymer, disposed over all or a portion of the substrate. The copolymer contains one or more polymer chains, within which isobutylene and at least one elevated $T_g$ monomer (and, optionally, other monomers) are incorporated in a random, periodic, statistical or gradient distribution.

As used herein a "layer" of a given material is a layer of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

In certain embodiments, the medical device further comprises at least one therapeutic agent. If desired, the polymeric layer can function as a release layer in these embodiments. Release layers for use in accordance with the present invention include carrier layers and barrier layers. By "carrier layer" is meant a release layer which further comprises a therapeutic agent and from which the therapeutic agent is released. By "barrier layer" is meant a layer which is disposed between a source of therapeutic agent and a site of intended release, and which controls the rate at which the therapeutic agent is released. For example, in some embodiments, the medical device substrate is the source of therapeutic agent. In other embodiments, the barrier layer is disposed over a source of therapeutic agent, which is in turn disposed over the medical device substrate.

Medical devices for use in conjunction with the present invention include essentially any medical device for which controlled release of a therapeutic agent is desired. Examples of medical devices include implantable or insertable medical devices, for example, catheters (e.g., renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, and any coated substrate (which can comprise, for example, glass, metal, polymer, ceramic and combinations thereof) that is implanted or inserted into the body and from which therapeutic agent is released. Examples of medical devices further include patches for delivery of therapeutic agent to intact skin and broken skin (including wounds); sutures, suture anchors, anastomosis clips and rings, tissue staples and ligating clips at surgical sites; orthopedic fixation devices such as interference screws in the ankle, knee, and hand areas, tacks for ligament attachment and meniscal repair, rods and pins for fracture fixation, screws and plates for craniomaxillofacial repair; dental devices such as void fillers following tooth extraction and guided-tissue-regeneration membrane films following periodontal surgery; and tissue engineering scaffolds for cartilage, bone, skin and other in vivo tissue regeneration.

The medical devices of the present invention include medical devices that are used for either systemic treatment or for the localized treatment of any mammalian tissue or organ. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, vagina, uterus, ovary, and prostate; skeletal muscle; smooth muscle; breast; dermal tissue; cartilage; and bone.

Specific examples of medical devices for use in conjunction with the present invention include vascular stents that deliver therapeutic agent into the vasculature for the treatment of restenosis. In these embodiments, a release layer is typically provided over all or a portion of a stent substrate, more typically in the form of a carrier layer (in which case the therapeutic agent is disposed within the release layer) or a barrier layer (in which case the release layer is disposed over a therapeutic-agent containing layer).

As used herein, "treatment" refers to the prevention of a disease or condition, the reduction or elimination of symptoms associated with a disease or condition, or the substantial or complete elimination of a disease or condition. Preferred subjects are mammalian subjects and more preferably, human subjects.

As noted above, copolymers for use in the medical devices of the present invention contain one or more polymer chains, which in turn contain isobutylene and one or more elevated $T_g$ monomers (and, optionally, other monomers). These monomers are incorporated into the polymer chains in a random, periodic, statistical or gradient distribution. As used herein, a polymer "chain" is a linear grouping of 10 or more constitutional units, commonly 20 or more, 50 or more, 100 or more, 200 or more, 500 or more, or even 1000 or more units.

An "elevated $T_g$ monomer" is a monomer that can display a $T_g$, as measured by any of a number of techniques including differential scanning calorimetry (DSC), dynamic mechanical analysis (DMA), or dielectric analysis (DEA), that is above ambient temperature, more typically above 50° C., above 60° C., above 70° C., above 80° C., above 90° C. or even above 100° C., when the monomer is in homopolymer form. "Ambient temperature" is typically below 25° C.-45° C., more typically body temperature (e.g., about 35° C.-40° C.). Hence, "elevated $T_g$ monomers" do not include monomers which do not exist in and of themselves as homopolymers, e.g., maleic anhydride.

In some preferred embodiments, the elevated $T_g$ monomer, in its polymerized form, is biostable. A "biostable" polymer is one which remains associated with the medical device during its period of residence within a patient.

Examples of monomers that can exhibit an elevated $T_g$ when in homopolymer form include, for example, vinyl aromatic monomers, other vinyl monomers, other aromatic monomers, methacrylic monomers, acrylic monomers, and alkenes.

Vinyl aromatic monomers are those having aromatic and vinyl moieties and include unsubstituted monomers, vinyl-substituted monomers and ring-substituted monomers. Suitable vinyl aromatic monomers include the following (listed along with a published homopolymer $T_g$ and, in some instances, a published homopolymer melting point $T_m$): (a) unsubstituted vinyl aromatics, such as atactic styrene ($T_g$ 100° C.), isotactic styrene ($T_g$ 100° C.) ($T_m$ 240° C.) and 2-vinyl naphthalene ($T_g$ 151° C.), (b) vinyl substituted aromatics such as α-methyl styrene, (c) ring-substituted vinyl aromatics including (i) ring-alkylated vinyl aromatics such as 3-methylstyrene ($T_g$ 97° C.), 4-methylstyrene ($T_g$ 97° C.), 2,4-dimethylstyrene ($T_g$ 112° C.), 2,5-dimethylstyrene ($T_g$ 143° C.), 3,5-dimethylstyrene ($T_g$ 104° C.), 2,4,6-trimethylstyrene ($T_g$ 162° C.), and 4-tert-butylstyrene ($T_g$ 127° C.), (ii) ring-alkoxylated vinyl aromatics, such as 4-methoxystyrene ($T_g$ 113° C.) and 4-ethoxystyrene ($T_g$ 86° C.), (iii) ring-halogenated vinyl aromatics such as 2-chlorostyrene ($T_g$ 119° C.), 3-chlorostyrene ($T_g$ 90° C.), 4-chlorostyrene ($T_g$ 110° C.), 2,6-dichlorostyrene ($T_g$ 167° C.), 4-bromostyrene ($T_g$ 118° C.) and 4-fluorostyrene ($T_g$ 95° C.) and (iv) ester-substituted vinyl aromatics such as 4-acetoxystyrene ($T_g$ 116° C.).

Other suitable vinyl monomers include the following: (a) vinyl alcohol ($T_g$ 85° C.) ($T_m$ 220° C.); (b) vinyl esters such as vinyl benzoate ($T_g$ 71° C.), vinyl 4-tert-butyl benzoate ($T_g$ 101° C.), vinyl cyclohexanoate ($T_g$ 76° C.), vinyl pivalate ($T_g$ 86° C.), vinyl trifluoroacetate ($T_g$ 46° C.), vinyl butyral ($T_g$ 49° C.) ($T_m$ 322° C.), (c) vinyl amines such as 2-vinyl pyridine ($T_g$ 104° C.), 4-vinyl pyridine ($T_g$ 142° C.), and vinyl carbazole ($T_g$ 227° C.) ($T_m$ 320° C.), (d) vinyl halides such as vinyl chloride ($T_g$ 81° C.) ($T_m$ 227° C.) and vinyl fluoride ($T_g$ 40° C.) ($T_m$ 171° C.); (e) alkyl vinyl ethers such as methyl vinyl ether ($T_g$ −31° C.) ($T_m$ 144° C.), propyl vinyl ether ($T_g$ −49° C.) ($T_m$ 76° C.), butyl vinyl ether ($T_g$ −55° C.) ($T_m$ 64° C.), isobutyl vinyl ether ($T_g$ −19° C.) ($T_m$ 165° C.), tert-butyl vinyl ether ($T_g$ 88° C.) ($T_m$ 250° C.) and cyclohexyl vinyl ether ($T_g$ 81° C.), and (f) other vinyl compounds such as 1-vinyl-2-pyrrolidone ($T_g$ 54° C.) and vinyl ferrocene ($T_g$ 189° C.).

Suitable aromatic monomers, other than the above vinyl aromatics, include acenaphthalene ($T_g$ 214° C.) and indene ($T_g$ 85° C.).

Suitable methacrylic monomers include (a) methacrylic acid ($T_g$ 228° C.), (b) methacrylic acid salts such as sodium methacrylate ($T_g$ 310° C.), (c) methacrylic acid anhydride ($T_g$ 159° C.), (d) methacrylic acid esters (methacrylates) including (i) alkyl methacrylates such as atactic methyl methacrylate ($T_g$ 105-120° C.), syndiotactic methyl methacrylate ($T_g$ 115° C.) ($T_m$ 200° C.), ethyl methacrylate ($T_g$ 65° C.), isopropyl methacrylate ($T_g$ 81° C.), isobutyl methacrylate ($T_g$ 53° C.), t-butyl methacrylate ($T_g$ 118° C.) and cyclohexyl methacrylate ($T_g$ 92° C.), (ii) aromatic methacrylates such as phenyl methacrylate ($T_g$ 110° C.) and including aromatic alkyl methacrylates such as benzyl methacrylate ($T_g$ 54° C.), (iii) hydroxyalkyl methacrylates such as 2-hydroxyethyl methacrylate ($T_g$ 57° C.) and 2-hydroxypropyl methacrylate ($T_g$ 76° C.), (iv) additional methacrylates including isobornyl methacrylate ($T_g$ 110° C.) and trimethylsilyl methacrylate ($T_g$ 68° C.), and (e) other methacrylic-acid derivatives including methacrylonitrile ($T_g$ 120° C.).

Suitable acrylic monomers include (a) acrylic acid ($T_g$ 105° C.), its anhydride and salt forms, such as potassium acrylate ($T_g$ 194° C.) and sodium acrylate ($T_g$ 230° C.); (b) certain acrylic acid esters such as isopropyl acrylate ($T_g$ −11° C.) ($T_m$ 162° C.), tert-butyl acrylate ($T_g$ 43-107° C.) ($T_m$ 193° C.), hexyl acrylate ($T_g$ 57° C.) and isobornyl acrylate ($T_g$ 94° C.); (c) acrylic acid amides such as acrylamide ($T_g$ 165° C.), N-isopropylacrylamide ($T_g$ 85-130° C.) and N,N dimethylacrylamide ($T_g$ 89° C.); and (d) other acrylic-acid derivatives including acrylonitrile ($T_g$ 125° C.) ($T_m$ 319° C.).

Suitable alkene based monomers include the following: ethylene (HDPE) ($T_g$ −125° C.) ($T_m$ 130° C.), isotactic propylene ($T_g$ −8° C.) ($T_m$ 176° C.), 4-methyl pentene ($T_g$ 29° C.) ($T_m$ 250° C.), 1-octadecene ($T_g$ 55° C.), and tetrafluoroethylene ($T_g$ 117° C.) ($T_m$ 327° C.).

The copolymers of the present invention may be present in a variety of configurations, including cyclic, linear and branched configurations. Branched configurations include radial configurations (e.g., star configurations in which three or more polymer chains emanate from a single branch point), comb configurations (e.g., configurations having a main chain and a plurality of side polymer chains) and dendritic configurations (e.g., arborescent and hyperbranched polymers).

The copolymers can be synthesized using a variety of synthetic schemes including, for example, living cationic polymerization, quasi-living cationic polymerization, non-living cationic polymerization, living radical polymerization, quasi-living radical polymerization, and non-living radical polymerization.

As will be appreciated by those of ordinary skill in the art, the copolymers described herein, including those described in the preceding paragraphs, may be recovered from the reaction mixtures by any of the usual techniques, including but not limited to, evaporation of solvent, precipitation with a non-solvent, such as an alcohol or alcohol/acetone mixture, followed by drying, and so forth. In addition, purification of the copolymer can be performed, for example, by sequential extraction in aqueous media, both with and without the presence of various alcohols, ethers and ketones.

The polymeric layers and other compositions of the present invention optionally include a supplemental polymer in addition to the above-described copolymers. A variety of polymers are available for this purpose. For example, the supplemental polymer may be a homopolymer or a copolymer (including alternating, random, tapered, statistical, gradient and block copolymers), it may be cyclic, linear or branched in architecture (e.g., polymers having star, comb or dendritic architecture), it may be natural or synthetic, or it may be thermoplastic or thermosetting, and so forth. For example, a polystyrene-random-polyisobutylene copolymer in accordance with the present invention can be blended with a biodisintegratable homopolymer or copolymer.

Supplemental polymers for the practice of the invention may be selected, for example, from the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

Numerous techniques are available for forming the polymeric layers and other compositions of the present invention. For example, where the selected copolymer (and supplemental polymer, if any) has thermoplastic characteristics, a variety of standard thermoplastic processing techniques can be used to form the polymeric layers and other compositions, including compression molding, injection molding, blow molding, spinning, vacuum forming and calendaring, as well as extrusion into sheets, tubes and other cross-sectional profiles of various lengths. For example, using these techniques, a coating can be provided by extruding a coating layer onto a pre-existing stent substrate. As yet another example, a coating can be co-extruded along with an underlying stent body.

If a therapeutic agent is to be added and it is stable at processing temperatures, then it can be combined with the copolymer prior to thermoplastic processing, to produce a therapeutic-agent-containing layer or other therapeutic-agent-containing composition. If not, then a therapeutic-agent-containing layer or other therapeutic-agent-containing composition can nonetheless be formed by subsequent introduction of therapeutic agent, for example, as discussed below.

Polymeric layers and other compositions in accordance with the present invention can also be formed using solvent-based techniques in which the copolymer (and supplemental polymer, if any) is first dissolved or dispersed in a solvent and the resulting mixture is subsequently used to form the polymeric layer or other composition.

Where solvent-based techniques are used, the solvent system that is selected will contain one or more solvent species. The solvent system preferably is a good solvent for the copolymer and, where included, for the supplemental polymer and therapeutic agent as well. The particular solvent species that make up the solvent system may also be selected based on other characteristics including drying rate and surface tension.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments, a mixture containing solvent, copolymer and supplemental polymer, if any, is applied to a substrate to form a release layer. For example, the substrate can be all or a portion of an implantable or insertable medical device, such as a stent, to which a release layer is applied. The substrate materials used for making stents typically comprise steel and other metals and alloys as well as polymeric and/or plastic materials. These and other materials are within the scope of this invention.

Where appropriate, techniques such as those listed above can be repeated or combined to build up a release layer or other composition to a desired thickness. The thickness of the layer or composition can be varied in other ways as well. For example, in one beneficial process, solvent spraying, the coating thickness can be increased by modification of coating process parameters, including increasing spray flow rate, slowing the movement between the substrate to be coated and the spray nozzle, providing repeated passes and so forth.

Where a carrier layer or other therapeutic-agent containing composition is formed, a therapeutic agent can be dissolved or dispersed in the polymer/solvent mixture if desired, and hence co-established with the carrier layer or other therapeutic-agent containing composition. In other embodiments, a carrier layer or other therapeutic-agent containing composition can be formed by dissolving or dispersing a therapeutic agent in a solvent, and the resulting solution contacted with a polymeric layer or other composition that is previously formed using, for example, one or more of the application techniques described above (e.g., dipping, spraying, etc.).

Barrier layers, on the other hand, are formed over a therapeutic-agent containing region, for example, using solvent-based techniques such as those discussed above in which the copolymer and supplemental polymer, if any, are first dissolved or dispersed in a solvent, and the resulting mixture is subsequently used to form the barrier layer. Where the release characteristic of the underlying therapeutic-agent containing region may resemble a burst/plateau (e.g., instead of a linear release profile), the barrier layer may serve, for example, as a boundary layer to retard diffusion of the therapeutic agent, and aid to prevent a burst phenomenon, whereby much of the therapeutic agent is released immediately upon exposure of the device or a portion of the device to the implant or insertion site.

In some embodiments, a therapeutic-agent containing region is provided beneath a barrier layer, which comprises one or more polymers such as those described elsewhere herein. The polymeric composition of the barrier layer may, or may not, be the same as the polymeric composition of the underlying therapeutic-agent containing region. The therapeutic-agent containing region can be established using thermoplastic and solvent-based techniques (e.g., dipping, spraying, etc.) such as those discussed above.

In other embodiments, a therapeutic-agent containing region is established beneath the barrier layer without an associated polymer. In these cases, for example, the therapeutic agent can simply be dissolved or dispersed in a solvent or liquid, and the resulting solution/dispersion can be contacted with a substrate again using, for instance, one or more of the above-described application techniques.

Where the release layer or other composition is formed using a solvent-based technique, it is preferably dried after application to remove the solvents. Where formed, a release layer typically further conforms to any underlying surface during the drying process.

"Therapeutic agents," "pharmaceutically active agents," "pharmaceutically active materials," "drugs," and other related terms may be used interchangeably herein and include genetic therapeutic agents, non-genetic therapeutic agents and cells. Therapeutic agents may be used singly or in combination. Therapeutic agents may be used singly or in combination. Therapeutic agents may be, for example, nonionic or they may be anionic and/or cationic in nature.

Exemplary non-genetic therapeutic agents for use in connection with the present invention include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (O) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (O) agents that interfere with endogenous vasoactive mechanisms; (p) inhibitors of leukocyte recruitment, such as monoclonal antibodies; (q) cytokines; (r) hormones; and (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin.

Preferred non-genetic therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomycin D, Resten-NG, Ap-17, abciximab, clopidogrel and Ridogrel, among others.

Exemplary genetic therapeutic agents for use in connection with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers such as polyvinylpyrrolidone (PVP), SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Therapeutic agents also include ablation agents, sufficient amounts of which will result in necrosis (death) of undesirable tissue, such as malignant tissue, prostatic tissue, and so forth. Examples include osmotic-stress-generating agents, for example, salts such as sodium chloride or potassium chloride; organic solvents, particularly those such as ethanol, which are toxic in high concentrations, while being well tolerated at lower concentrations; free-radical generating agents, for example, hydrogen peroxide, potassium peroxide or other agents that can form free radicals in tissue; basic agents such as sodium hydroxide; acidic agents such as acetic acid and formic acid; enzymes such as collagenase, hyaluronidase, pronase, and papain; oxidizing agents, such as sodium hypochlorite, hydrogen peroxide or potassium peroxide; tissue fixing agents, such as formaldehyde, acetaldehyde or glutaraldehyde; and naturally occurring coagulants, such as gengpin.

A wide range of therapeutic agent loadings can be used in connection with the dosage forms of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

The release profile associated with the release layer or other composition can be modified in a number of ways, including, for example, (a) changing the molecular weight of the copolymer, (b) changing the configuration of the copolymer (e.g., a linear copolymer vs. a branched copolymer), (c) changing the ratio of the isobutylene monomer to the elevated $T_g$ monomer in the copolymer, (d) changing the elevated $T_g$ monomer (e.g., by substituting or adding an elevated $T_g$ monomer of increased or decreased hydrophilicity, (e) by blending one or more supplementary polymers with the copolymer, (f) by varying the thickness of the release layer or other composition, and so forth.

For example, the release profile of the therapeutic agent can be modified by increasing or decreasing the overall hydrophilicity of the copolymer (or, viewed conversely, decreasing or increasing the overall hydrophobicity).

The release profile associated with release layers in accordance with the present invention can also be modified by changing the number, order, thickness, or position of carrier and barrier layers with respect to one another. For example, the release profile can be modified by varying the thickness of the release layer. Moreover, multiple release layers can be employed to modify the release profile, for example, (a) a barrier layer containing the copolymer of the invention can be positioned over a carrier layer containing the copolymer of the invention and a therapeutic agent, (b) multiple carrier layers of the invention, either of the same or different content (e.g., different polymer and/or therapeutic agent content) can be stacked on top of one another, either with or without intervening barrier layers, (c) multiple carrier layers of the invention of differing compositions can be positioned laterally to one another, and so forth. In addition, where a carrier layer is employed, a therapeutic-agent concentration gradient can be established within the carrier layer to control release of therapeutic agent.

As indicated above, the release profile associated with release layers in accordance with the present invention can be modified, for example, by altering the chemical composition of the release layer (e.g., by changing the chemical composition of the copolymer or by blending one or more supplementary polymers with the copolymer).

Hence, in certain embodiments of the present invention, the drug release rate of the therapeutic releasing agent is controlled by changing the hydrophilic/hydrophobic ratio of the copolymer of the present invention by the incorporation of one or more hydrophilic or hydrophobic monomers such that the overall hydrophilicity of the copolymer is increased or decreased (or, viewed conversely, the overall hydrophobicity is increased or decreased). As will be appreciated by one of skill in the art, the ratio may be changed in a number of ways.

In some aspects, the hydrophilicity of the copolymer can be increased by forming copolymers with one or more hydrophilic monomers, including those numerous examples of hydrophilic monomers specifically listed above as elevated $T_g$ monomers (e.g., hydroxyethylmethacrylate monomer). In alternative embodiments, the hydrophobicity of the resulting copolymer is increased by forming copolymers with one or more hydrophobic monomers. Any one or more of a number of hydrophobic monomers can be used, including those numerous examples of hydrophobic monomers specifically listed above as elevated $T_g$ monomers (e.g., alkyl methacrylate monomers).

Although one of skill in the art would readily discern whether a monomer is predominantly hydrophilic or hydrophobic, various monomers having hydrophilic or hydrophobic characteristics and which are suitable for use in the present invention and which can be used to modulate the hydrophilic and/or hydrophobic character of the materials of the present invention are exemplified, but not limited by the following: (1) hydrophobic monomers, including vinyl aromatic monomers such as unsubstituted vinyl aromatics, vinyl substituted aromatics, ring-substituted vinyl aromatics; vinyl esters; vinyl halides; alkyl vinyl ethers; and other vinyl compounds such as vinyl ferrocene; aromatic monomers other than vinyl aromatics, including acenaphthalene and indene; acrylic monomers including acrylic acid esters such as alkyl acrylates, arylalkyl acrylates, alkoxyalkyl acrylates, haloalkyl acrylates, cyano-alkyl acrylates and other acrylic-acid derivatives including acrylonitrile; methacrylic monomers, including methacrylic acid esters (methacrylates) such as alkyl methacrylates and aminoalkyl methacrylates and other methacrylic-acid derivatives including methacrylonitrile; alkene-based monomers, including ethylene, isotactic propylene, 4-methyl pentene, 1-octadecene, and tetrafluoroethylene and other unsaturated hydrocarbon monomers; cyclic ether monomers; ether monomers other than alkoxyalkyl acrylates and methacrylates; and other monomers including epsilon-caprolactone; and (2) hydrophilic monomers, including vinyl amines, alkyl vinyl ethers such as methyl vinyl ether, 1-vinyl-2-pyrrolidone and other vinyl compounds; methacrylic monomers including methacrylic acid and methacrylic acid salts; acrylic monomers such as acrylic acid, its anhydride and salt forms, and acrylic acid amides; and cyclic ether monomers such as ethylene oxide.

In this connection, in some preferred embodiments, the copolymer may contain one or more hydrophilic chains which comprise one or more hydrophilic monomers (such as polymer chains containing ethylene oxide or vinylpyrrolidone), either singly as homopolymer chains, or in combination as copolymer chains, for instance, arranged in a repeating (e.g., alternating), random, statistical or gradient distribution. In other preferred embodiments, the copolymer may contain one or more hydrophobic chains, comprising one or more hydrophobic monomers (such as polymer chains containing methylmethacrylate or polystyrene), either singly or in combination. The copolymer may also contain one or more chains that comprise a combination of both hydrophilic and hydrophobic monomers, for instance, arranged in a repeating (e.g., alternating), random, statistical or gradient distribution. The hydrophilic and/or hydrophobic monomers can be selected from various monomer species, including but not limited to those numerous monomers specifically listed above.

In certain embodiments, the drug release rate is controlled by blending hydrophobic or hydrophilic polymers with the copolymers described herein in the release layers and other compositions of the invention, thereby increasing the hydrophobicity or hydrophilicity, respectively, of the release layers and compositions. In one exemplary embodiment, the invention provides a blend comprising a copolymer in accordance with the invention, which is blended with a hydrophilic polymer, such as poly(2-hydroxyethyl methacrylate), poly(2-vinyl pyridine), or a combination of hydrophilic polymers.

As will be appreciated by one of ordinary skill in the art, the copolymers of the present invention may be synthesized according to known methods, including non-living, quasi-living or living, cationic, anionic or non-ionic polymerizations and, in particular, radical polymerization methods such as azobis(isobutyronitrile)-initiated or peroxide-initiated processes, and controlled/"living" radical polymerizations such as metal-catalyzed atom transfer radical polymerization (ATRP), stable free-radical polymerization (SFRP), nitroxide-mediated processes (NMP), and degenerative transfer (e.g., reversible addition-fragmentation chain transfer (RAFT)) processes. These methods are well-detailed in the literature and are described, for example, in an article by Pyun and Matyjaszewski, "Synthesis of Nanocomposite Organic/Inorganic Hybrid Materials Using Controlled/" Living" Radical Polymerization," *Chem. Mater.*, 13:3436-3448 (2001), the contents of which are incorporated by reference in their entirety.

Such standard synthesis techniques are used to produce the copolymers of the present invention, which, in a preferred embodiment, comprise polyisobutylene and a hydrophobic polymer such as polystyrene in a random, periodic, statistical or gradient distribution.

Example 1

Synthesis of Polystyrene-Random-Polyisobutylene Copolymer

A polystyrene-random-polyisobutylene copolymer is synthesized using known cationic polymerization techniques. All of the experiments are carried out in 75 mL culture tubes in a solvent mixture comprising methylcyclohexane (MeChx) and monomer/$CH_3Cl$ (60/40 v/v) at $-80°$ C. Two different co-initiators are used for the polymerization process: (1) $TiCl_4$ and (2) $MeAlCl_2$.

As is well known by those of skill in the art of cationic chemistry, all solvents and reactants should be moisture, acid and inhibitor-free. Therefore, it may be necessary, depending upon the grade of material purchased, to distill these chemicals or flow them through columns containing drying agents, inhibitor removers and the like, prior to introducing them into the reaction procedure.

For instance, methyl chloride ($CH_3Cl$) and isobutylene (Matheson) are passed through in-line gas purifier columns packed with BaO/Drierite and condensed at $-80°$ C. prior to polymerization. Methylcyclohexane (MeChx) (Aldrich, anhydrous grade), titanium (IV) chloride (Aldrich, 99.9%), 2,6-di-tert-butylpyridine (DTBP)(Aldrich, 97%), and methylaluminum dichloride (Aldrich, 1.0 M in hexane) are used as received. Styrene (Aldrich, 99%) is purified by washing with 10% aqueous sodium hydroxide solution followed by distilled water until it is neutral and then dried over $Na_2SO_4$. It is distilled from calcium hydride under vacuum. 5-tert-Butyl-1,3-bis(1-chloro-1 methylethyl)benzene (tBuDiCumCl) is prepared from the corresponding alcohol, 5-tert-butyl-1,3-bis(1-hydroxy-1-methylethyl)benzene by hydrochlorination.

1. Polymerization with $TiCl_4$ Coinitiator

The following concentrations are used in the polymerization: [t-BuDiCumCl]=0.001 M, [DTBP]=0.004 M, [IB]=1.291 M, [St]=0.264 M, MeChx+IB+St/MeCl=60/40, [$TiCl_4$]=0.108 M. The reagents are added in this order: MeChx (10.2 mL at room temperature), MeCl (9.2 mL), t-BudiCumCl (1.0 mL, 0.025 M in MeChx), DTBP (1.0 mL, 0.10 M in MeChx), isobutylene (2.52 mL), styrene (0.76 mL) and $TiCl_4$ (1.0 mL, 2.7 M in MeChx/MeCl=60/40).

Specifically, hexanes (e.g., MeChx) are discharged into a dried, airtight reactor, containing cooling coils and a cooling jacket. The reactor with the hexanes is cooled with liquid nitrogen or other heat transfer media. Methyl chloride is condensed into the reactor by bubbling the gas through the cooled hexanes, followed by the addition of t-BudiCumCl, flushing with hexanes. Next, di-tert-butyl-pyridine is mixed with MeChx and added to the tank, followed by flushing with further hexanes. Isobutylene is charged and condensed into the reactor by bubbling the gas through the cooled solvent system. Styrene is added, followed by sufficient hexanes to bring total hexane weight in the mixing tank to the desired amount. The temperature is then brought to about $-80°$ C. and maintained at that temperature. The polymerization is initiated by the addition of $TiCl_4$, which is charged and added to the reactor.

The components are stirred thoroughly and left to polymerize for approximately 15 to 45 minutes. The polymerization is terminated by the addition of prechilled methanol to the reactor, and the polymer is precipitated into excess methanol (~60 mL). The precipitation is repeated from tetrahydrofuran (THF) into methanol.

The reactor is then allowed to warm to room temperature while being aware of any pressure increases, and the methyl chloride is removed from the reactor by boiling it and condensing it into a chilled collection tank. An additional amount of hexanes or other solvent, such as tetrahydrofuran or toluene is added to the reactor to replace the removed methyl chloride. These additional solvents are used to solubilize the polymer to enable it to be drained out of the reactor, as otherwise the polymer may become too thick to readily flow. The copolymer solution from the reactor is then precipitated in methanol (equal in weight to the initial copolymer/hexanes to be coagulated). The precipitated polymer is then poured into a sieve, the polymer removed and dried in a vacuum oven for at least 24 hours at approximately $125°$ C. under full vacuum.

2. Polymerization with $MeAlCl_2$ Coinitiator

In a separate set of polymerizations, $MeAlCl_2$ is used as the coinitiator instead of $TiCl_4$. The following concentrations are used in the polymerization: [t-BuDiCumCl]=0.001 M, [DTBP]=0.006 M, [IB]=1.242 M, [St]=0.288 M, MeChx+IB+St/MeCl=60/40, [$MeAlCl_2$]=0.01 M. The reagents are added in the following order: MeChx (10.6 mL at room temperature), MeCl (10.0 mL), t-BudiCumCl (1.0 mL, 0.025 M in MeChx), DTBP (1.0 mL, 0.15 M in MeChx), isobutylene (2.42 mL), styrene (0.83 mL) and $MeAlCl_2$ (0.25 mL 1.0 M in hexane). As described above for the experiments using $TiCl_4$ as the coinitiator, the components are stirred thoroughly and left to polymerize. The polymerization is terminated by prechilled methanol, and the polymer is precipitated into excess methanol (~60 mL). The precipitation is repeated from THF into methanol.

3. Characterization

Molecular weights are measured with a Waters HPLC system equipped with a model 510 HPLC pump, model 410 differential refractometer, model 441 absorbance detector, on-line multiangle laser light scattering (MALLS) detector (MiniDawn, Wyatt Technology Inc.), Model 712 sample processor, and five Ultrastyragel GPC columns connected in the following series: 500, $10^3$, $10^4$, $10^5$, and 100 Å. THF is used as a carrier solvent with a flow rate of 1 mL/min.

For the polymerization utilizing $TiCl_4$ as the coinitiator, the yield is 85.6%, the $M_n$=66,600 and the polydispersity index (PDI)=1.18. In the polymerization utilizing $MeAlCl_2$ as the coinitiator, the yield is 86.2%, the $M_n$=50,200, and the PDI=1.57.

Example 2

Stent Coatings

1. Preparation of Coatings

The solvent system selected for use in such a procedure will depend upon the nature of the copolymer and therapeutic agent selected. In the case of a polystyrene-random-polyisobutylene copolymer with paclitaxel as therapeutic agent, a preferred solution is one containing (1) between about 0-94 wt %, preferably, 94 wt %, toluene, (2) between about 5 wt %-99 wt %, preferably 5 wt %, tetrahydrofuran and (3) 1 wt % of the copolymer and paclitaxel combined.

The following polymer solutions are made: (1) a solution containing 99 wt % solvent (5 wt % THF, 94 wt % toluene), 0.75 wt % of polystyrene-random-polyisobutylene copolymer and 0.25 wt % paclitaxel; (2) a solution containing 99 wt % solvent (5 wt % THF, 94 wt % toluene), 0.912 wt % polystyrene-random-polyisobutylene copolymer and 0.088 wt % paclitaxel; (3) a solution containing 99 wt % solvent (5 wt % THF, 94 wt % toluene), 0.75 wt % polystyrene-polyisobutylene-polystyrene triblock copolymer (SIBS) (as described in U.S. Pat. No. 6,545,097, entitled "Drug delivery compositions and medical devices containing block copolymer") and 0.25 wt % paclitaxel; and (4) a solution containing 99 wt % solvent (5 wt % THF, 94 wt % toluene), 0.912 wt % polystyrene-polyisobutylene-polystyrene triblock copolymer (SIBS) and 0.088 wt % paclitaxel.

All solutions are prepared by mixing the polymer with the toluene and heating to 70° C. for about an hour, cooling to room temperature, adding the THF, adding the paclitaxel, thoroughly mixing (e.g., overnight), and filtering.

For solutions (1) and (2), above, the styrene is copolymerized with the isobutylene to produce random copolymers wherein the styrene comprises either 16.7 mole % or 17.6 mole % of the copolymer, and which have number average molecular weights (Mn) of 49,300 g/mole (PDI=0.45) and 41,900 g/mole (PDI=1.74), respectively. For solutions (3) and (4), the polystyrene-polyisobutylene-polystyrene triblock copolymer has an Mn of 103,500 g/mole and a styrene content of 16.9 mol %.

Each solution is then placed in a syringe pump and fed to a spray nozzle. A stent is mounted onto a holding device parallel to the nozzle and rotated to ensure uniform coverage. Depending on the spray equipment used, either the stent or spray nozzle can be moved while spraying such that the nozzle moves along the stent while spraying for one or more passes. After a carrier coating is formed in this fashion, the stent is dried, for example, by placing it in a preheated oven for 30 minutes at 65° C., followed by 3 hours at 70° C. Eight stents are formed in this manner for each of the solutions.

In another preferred process, solutions like those above containing 99% solvent and 1% combined copolymer and paclitaxel, is sprayed with an airbrush onto a rotating medical device component, such as a stent. The environment is controlled during spraying so that the solvent evaporates between the sprayer and the component, allowing a porous mat loaded with a therapeutic agent to be formed on the rotating component. Spraying is stopped when the desired coating thickness is achieved.

After a component or layer has been formed using one of the above solvent-based techniques, the component or layer can be dried, for example, by placing it in a preheated oven (e.g., for 30 minutes at 65° C., followed by 3 hours at 70° C.).

2. Paclitaxel Release from Stent Coatings

The release rate is controlled by varying the relative amounts of drug and copolymer. In addition, for a given amount of drug and copolymer, a difference in the kinetic release rate is observed in polymeric compositions containing the same constituents (e.g., polystyrene and polyisobutylene) but in two different morphological configurations (e.g., block and random distribution).

Figure 1:
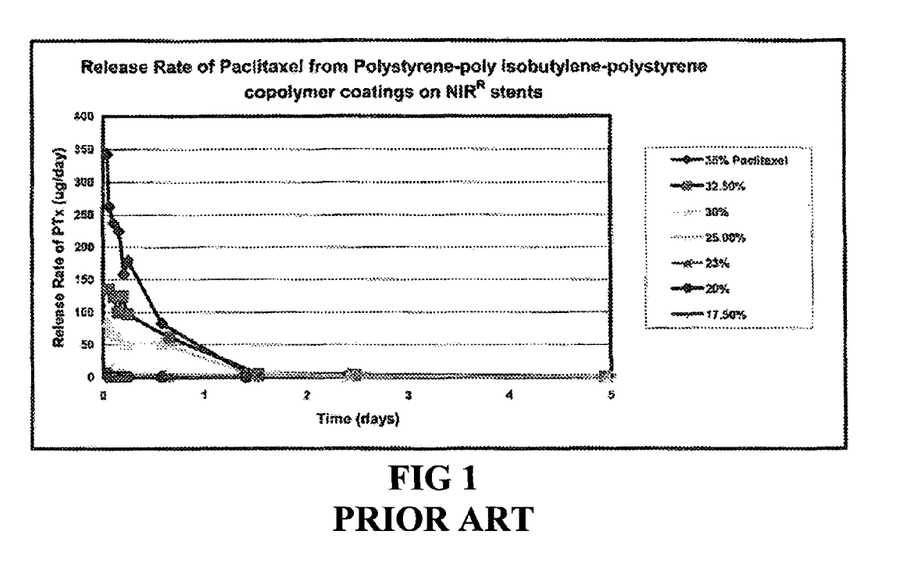
FIG. 1 graphically illustrates the kinetic release rate, measured as μg/day, of the therapeutic agent, paclitaxel, as a function of time for stents coated with a prior art block copolymer comprising polystyrene-polyisobutylene-polystyrene (SIBS) triblock copolymer at seven different paclitaxel loadings ranging from 0.175 wt % to 0.35 wt % of the copolymer composition.

In particular, FIG. 1 is taken from U.S. Pat. No. 6,545,097, cited above, and graphically illustrates the kinetic release rate, measured as μg/day, of the therapeutic agent, paclitaxel, as a function of time for stents coated with using polystyrene-polyisobutylene-polystyrene (SIBS) triblock copolymer at seven different paclitaxel loadings ranging from 0.175 wt % to 0.35 wt % of the copolymer composition. The coating formulations are made with 94 wt % toluene and 5 wt % tetrahydrofuran, with the remaining 1 wt % of the formulation being made up of paclitaxel and styrene-isobutylene-styrene copolymer in respective relative amounts of 35%-65%, 32.5%-67.5%, 30%-70%, 25%-75%, 22.5%-87.5%, 20%-80% and 17.5%-83.5% with an equivalent total coating weight. Coating thickness was about 16 microns. As previously reported in U.S. Pat. No. 6,545,097, the release rates in FIG. 1 range from a relatively rapid release in connection with the highest paclitaxel value (35%) to a relatively slow release at the lowest value (17.5%).

Figure 2:
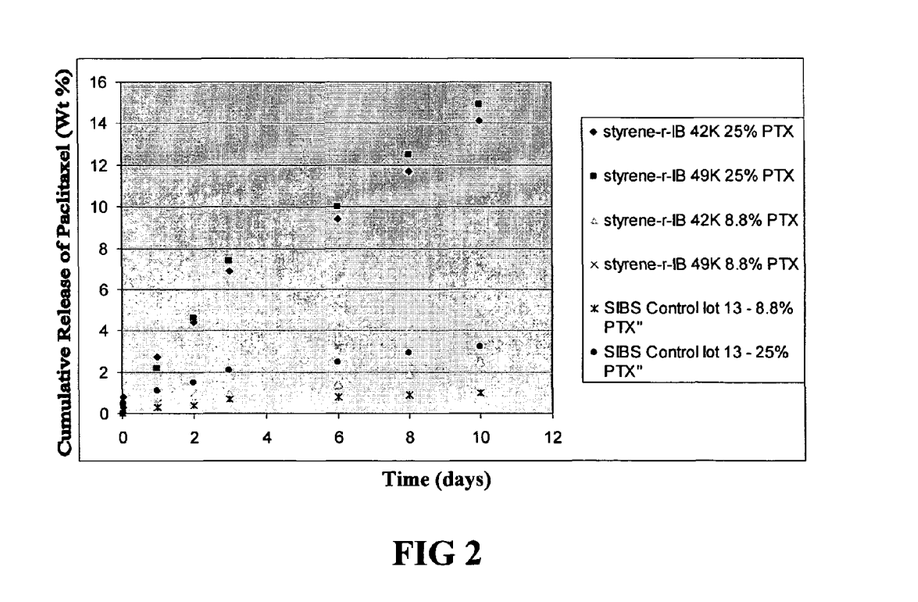
FIG. 2 graphically illustrates the kinetic release rate, measured as wt % of the total therapeutic load of the therapeutic agent, paclitaxel, as a function of time for stents coated with a copolymer comprising polystyrene-random-polyisobutylene at two separate molecular weight compositions, as compared with the prior art SIBS triblock copolymer.

In comparison, the release of paclitaxel from stent coatings prepared according to the present invention, composed of the same polymeric constituents (styrene and isobutylene) as the prior art coating of FIG. 1, exhibited different and enhanced drug release characteristics as measured as a function of time. FIG. 2 shows the kinetic release rate, presented as the cumulative release of paclitaxel as a function of time, in PBS containing 0.5 wt % Tween® 20 (polyoxyethylene(20) sorbitan monolaurate) available from Sigma-Aldrich for coatings formed using solutions (1), (2), (3) and (4) described above. FIG. 2 shows release data for 75% copolymer/25% paclitaxel and 91.2% copolymer/8.8% paclitaxel stent coatings prepared according to the present invention using polystyrene-random-polyisobutylene copolymer (random-SIB) at two different number average molecular weights (Mn=41,900 g/mole and Mn=49,300 g/mole). In addition, FIG. 2 also shows release data for a 75% copolymer/25% paclitaxel stent coating and a 91.2% copolymer/8.8% paclitaxel stent coating, prepared using the polystyrene-polyisobutylene-polystyrene (SIBS) triblock copolymer, as taught in U.S. Pat. No. 6,545,097. Whereas the SIBS triblock copolymer material showed less than a 4% cumulative release of the total paclitaxel load over a ten day period at a 25% paclitaxel/copolymer load and less than a 2% cumulative release at a 8.8% paclitaxel/copolymer load, the random-SIB copolymer material showed a release percentage of about 14% and 15% at a 25% paclitaxel load (Mn=41,900 g/mol and Mn=49,300 g/mol, respectively) and about 2% and 3% at a 8.8% paclitaxel load (Mn of polystyrene is 41,900 g/mol and 49,300 g/mol, respectively).

As shown in FIG. 2, the release of paclitaxel from the random copolymers of the present invention is virtually linear and sustained over the 10 day measurement period. This controlled release is observed at both 25% and 8.8% paclitaxel loading levels. The prior art SIBS triblock copolymer having approximately the same styrene content (16.9 mol %) showed a substantially lower release of paclitaxel and more of a burst-plateau profile at both 8.8% and 25% paclitaxel loadings.

Although various embodiments are specifically illustrated and described herein, it will be appreciated that modifications and variations of the present invention are covered by the above teachings and are within the purview of the appended claims without departing from the spirit and intended scope of the invention.

What is claimed is:

1. A medical device comprising (a) a substrate and (b) a polymeric carrier layer consisting of (i) a copolymer having a polymer chain in which styrene and isobutylene monomers are incorporated in a random distribution and (ii) a therapeutic agent, said copolymer being loaded with said therapeutic agent, wherein the cumulative release of the therapeutic agent after ten days from the polymeric carrier layer-composition is greater than the cumulative release after ten days from a polymeric carrier-composition in which a block copolymer having the same styrene and isobutylene monomers is substituted for the copolymer in an amount equal to the copolymer.

2. The device of claim 1, wherein said copolymer comprises a linear architecture.

3. The device of claim 1, wherein said copolymer comprises a branched architecture.

4. The device of claim 1, wherein said polymeric carrier layer is disposed over all of said substrate.

5. The device of claim 1, wherein said polymeric carrier layer is disposed over a portion of said substrate.

6. The device of claim 1, wherein said device further comprises a barrier layer that is disposed over said polymeric carrier layer.

7. The device of claim 1, wherein said medical device is an implantable or insertable medical device.

8. The device of claim 7, wherein said implantable or insertable medical device is selected from a catheter, a guide wire, a balloon, a filter, a stent, a stent graft, a vascular graft, a vascular patch and a shunt.

9. The device of claim 7, wherein said implantable or insertable medical device is adapted for implantation or insertion into the coronary vasculature, peripheral vascular system, esophagus, trachea, colon, biliary tract, urinary tract, prostate or brain.

10. A method of forming a coating on a medical device comprising:
a) providing a substrate that comprises a medical device;
b) providing a solution consisting of: a solvent system, a therapeutic agent, and a copolymer having a polymer chain in which styrene and isobutylene monomers are incorporated in a random distribution;
c) applying said solution to said substrate;
d) forming a polymeric carrier layer coating on said substrate by removing said solvent system from said solution;
wherein the cumulative release of the therapeutic agent after ten days from said polymeric carrier layer is greater than the cumulative release after ten days from a polymeric carrier in which a block copolymer having the same styrene and isobutylene monomers is substituted for said copolymer in an amount equal to the copolymer.

11. The device of claim 1, wherein the therapeutic agent is paclitaxel.

* * * * *